United States Patent [19]
Yankner

[11] Patent Number: 5,876,948
[45] Date of Patent: Mar. 2, 1999

[54] SCREENING METHODS TO IDENTIFY NEUROTOXIN INHIBITORS

[75] Inventor: Bruce A. Yankner, Boston, Mass.

[73] Assignee: The Children's Medical Center Corporation, Boston, Mass.

[21] Appl. No.: 737,371

[22] Filed: Jul. 29, 1991

Related U.S. Application Data

[63] Continuation-in-part of Ser. No. 559,173, Jul. 27, 1990, Pat. No. 5,137,873.

[51] Int. Cl.$^6$ .................................................. G01N 33/53
[52] U.S. Cl. ..................... 435/7.21; 435/7.9; 435/7.95; 435/40.5; 435/960; 436/519; 436/811
[58] Field of Search ..................................... 435/7.21, 7.9, 435/7.95, 29, 240.2, 960, 40.5; 436/518, 519, 811

[56] References Cited

U.S. PATENT DOCUMENTS

| | | |
|---|---|---|
| 3,862,114 | 1/1975 | Scandrett . |
| 4,059,693 | 11/1977 | Stewart . |
| 4,666,829 | 5/1987 | Glenner et al. . |

FOREIGN PATENT DOCUMENTS

WO 90/05138  5/1990  WIPO .

OTHER PUBLICATIONS

Guiroy et al, "Peptides Homologous to Amyloid Beta–Protein of Alzheimer's Disease Are Neurotoxic to Hippocampal Neurons in Vitro", Abstract 947B in Neurology, 40(Suppl. 1):373.

Yankner et al. "Neurotrophic and Neurotoxic Effects of Amyloid Protein: Reversal by Tachykinin Neuropeptides", Science, 250:279–282 (12 Oct. 1990).

Kowall et al. "An in vivo model for the neurodegenerative effects of β amyloid and protection by substance P", Proc. Natl. Acad. Sci. USA, 88:7247–7251 (Aug. 1991).

Beal et al., "Substance P–like immunoreactivity is reduced in Alzheimer's disease cerebral cortex," Neurology 37:1205–1208, 1987.

Bouras et al., "Substance P Immunoreactivity in Alzheimer Disease: A Study in Cases Presenting Symmetric or Asymmetric Cortical Atrophy," Alzheimer Disease and Associated Disorders 4:24–34, 1990.

Crystal et al., "Cortical Substance P–Like Immunoreactivity in Cases of Alzheimer's Disease and Senile Dementia of the Alzheimer Type," Journal of Neurochemistry 38:1781–1784, 1982.

Joachim et al., "Amuloid β–protein deposition in tissues other than brain in Alzheimer's disease," Nature 341:226–230, 1989.

Kang et al., "The precursor of Alzheimer's disease amyloid A4 protein resembles a cell–surface receptor," Nature 325:733–736, 1987.

Maggio, "Tachykinins," Ann. Rev. Neurosci. 11:13–28, 1988.

Quigley et al., "Substance P–Like Immunoreactive Neurons are Depleted in Alzheimer's Disease Cerebral Cortex," Neuroscience 41:41–60, 1991.

Robakis et al., "Molecular cloning and characterization of a cDNA encoding the cerebrovascular and the neuritic plaque amyloid peptides," Proc. Natl. Acad. Sci. USA 84:4190–4194, 1987.

Sisodia et al., "Evidence that β–Amyloid Protein in Alzheimer's Disease Is Not Derived by Normal Processing," Science 248:492–494, 1990.

Snider et al., "A Potent Nonpeptide Antagonist of the Substance P (NK1) Receptor," Science 251:435–437, 1991.

McLean et al., "Activity and Distribution of Binding Sites in Brain of a Nonpeptide Substance P (NK1) Receptor Antagonist," Science 251:437–439, 1991.

Wirak et al., "Deposits of Amyloid β Protein in the Central Nervous System of Transgenic Mice," Science 253:323–325, 1991.

Whitson et al., "Amyloid β Protein Enhances the Survival of Hippocampal Neurons in Vitro," Science 243:1488–1490, 1989.

Yankner et al., "Neurotoxicity of a Fragment of the Amyloid Precursor Associated with Alzheimer's Disease," Science 245:417–420, 1989.

*Primary Examiner*—Paula K. Hutzell
*Assistant Examiner*—Patricia A. Duffy
*Attorney, Agent, or Firm*—Fish & Richardson P.C.

[57] ABSTRACT

Method for treatment of a disease in a patient characterized by accumulation of β-amyloid. The method includes identifying a patient potentially suffering from such a disease and contacting a neuron of the patient with a therapeutically effective amount of a tachykinin agonist. Methods for screening for compounds useful for treating such a disease are also disclosed.

6 Claims, 4 Drawing Sheets

- ● β1-40 + Substance P
- ■ β1-40 + Physalaemin
- ▲ β1-40 + Neurokinin B
- □ β1-40 + Kassinin
- △ β1-40 + Eledoison
- ◇ β1-40 + Neurokinin A

SCREENING METHODS TO IDENTIFY NEUROTOXIN INHIBITORS

This application is a continuation-in-part of U.S. Ser. No. 08/559,173 filed Jul. 27, 1990 now U.S. Pat. No. 5,137,873 which is hereby incorporated by reference.

This invention was made with funding from the U.S. government; the U.S. government has rights in the invention.

BACKGROUND OF THE INVENTION

This invention relates to treating diseases characterized by an undesirable buildup of β-amyloid protein ("β-amyloid").

β-amyloid is a well characterized protein that is the primary constituent of senile plaques and cerebrovascular deposits in Alzheimer's disease and Down's syndrome. The form of β-amyloid that is most prevalent in senile plaques contains 40–42 amino acids, but various other β-amyloid forms are known, ranging from 28–43 amino acids in length.

β-amyloid protein is encoded as part of a message that encodes a much larger precursor (the amyloid precursor protein, APP), carboxy terminal fragments of which are neurotoxic to hippocampal neurons in culture. Yankner et al., 245 *Science* 417, 1989. Whitson et al., 243 *Science* 1488, 1989, however, describe a peptide homologous to β-amyloid which increases the survival of young undifferentiated hippocampal neurons in cell culture.

Patients with Alzheimer's disease exhibit reduced levels of neurotransmitter peptides: Beal et al., *Science* (1985) 229:289–291 (receptors for somatostatin); Davis et al., *Nature* (1980) 288:279–280 and Rossor et al., *Neurosci. Ltrs*. (1980) 20:373–377 (somatostatin); Whitehouse, et al. *Anal. Neurol*. (1981) 10:122–126 (acetyl choline); Quigley et al., *Neurosci* (1986) 17:70a and Quigley et al. (1991) *Neurosci* 41:41–60 (Substance P); Adolfsson et al. (1978) In "Alzheimer's Disease, Senile Dementia and Related Disorders (Aging)" Ed. Katzman et al., Vol. 7, pp. 441–451 New York, Rauer (noradrenalin).

SUMMARY OF THE INVENTION

Applicant has discovered that β-amyloid protein which accumulates abnormally in the brain is neurotoxic, and the deleterious effects of β-amyloid on neurons are selectively controlled or reversed by tachykinin agonists (e.g., those peptides having sequence similarity to specific tachykinins as discussed below). Accordingly, in a first aspect, the invention features a method for treatment or prophylaxis of neuronal accumulation of β-amyloid. The method includes identifying a patient potentially suffering from (or at risk for) such accumulation, and administering to the patient a therapeutically effective amount of a tachykinin agonist (defined below).

In preferred embodiments, the tachykinin agonist comprises a polypeptide region homologous to (e.g., a sequence at least three and preferably five or more amino acids in length from) substance P, physalaemin or neurokinin B. Specifically preferred agonists are Substance P, physalaemin and neurokinin B or derivatives (fragments or conservatively substituted sequences from) those three neurotransmitters. Useful tachykinin agonists and other therapeutics can also be identified by their ability to counteract β-amyloid accumulation on sensitive cells. Derivatives of Substance P (particularly N-terminal or C-terminal fragments or other derivatives) are particularly preferred, for example N-terminal Substance P fragments containing at least residues 1–4, or C-terminal fragments including amino acid residues 7–11. A particularly useful tachykinin agonist for use in the invention is the Substance P N-terminal fragment consisting of amino acid residues 1–7 ("Sub P [1–7]"). Other specific preferred fragments and derivatives are discussed below.

Specific Substance P derivatives or fragments, as well as other tachykinin agonists and other therapeutics for β-amyloid associated diseases can be identified by their ability to reduce the neurotoxic effect of a neurotoxic β-amyloid related polypeptide on cultured neurons, neuronal cell lines or other β-amyloid sensitive cells. Accordingly, a second aspect of the invention features methods for identifying compounds (such as tachykinin agonists) useful for treatment of diseases (such as Alzheimer's disease or Down's syndrome) that are characterized by accumulation of β-amyloid.

One such method includes providing a potentially therapeutic compound, providing a neurotoxin comprising β-amyloid or a derivative polypeptide which is neurotoxic and determining whether the potentially therapeutic compound reduces the neurotoxic effect of the neurotoxin on a cell that is sensitive to the neurotoxin. Preferred cells for use in this method are, e.g., primary neurons or cultured neuronal cell lines including cells of tissues that developmentally derive from nervous tissue, such as brain tissue and adrenal medulla. Other cell lines that respond to the β-amyloid polypeptide can be used. A reduction of β-amyloid related neurotoxicity by the potentially therapeutic compound is indicative that the compound is useful for treatment of the disease.

A second such method comprises providing the potentially therapeutic compound in combination with a cell-surface accumulating β-amyloid peptide, and determining whether accumulation of the β-amyloid peptide on the cell is reduced by the compound. Reduction of the β-amyloid peptide accumulation is indicative that the compound is useful for treatment of the disease. Preferably the accumulation of β-amyloid peptide on the cell is determined by immunohistochemical staining, e.g., using a β-amyloid antibody or by staining with thioflavin S or congo red. Alternatively, accumulation can be measured by measuring uptake of a radiolabeled amyloid into cell-surface amyloid accumulations.

Other preferred embodiments of the second aspect of the invention include administering the β-amyloid-related polypeptide to a sensitive cell and measuring the neurotoxic effect of the polypeptide on the cell; administering the potential therapeutic (e.g. a tachykinin agonist as described above) in combination with the neurotoxin to the cell and measuring the neurotoxic effect of that combination; and comparing the neurotoxic effects of the neurotoxin alone with that of the combination.

While cultured cells can be used in the second aspect of the invention, it is also possible to conduct in vivo determinations by intracerebral injection into a mammal (e.g. rodents or primates) of the neurotoxin, in the presence or absence of the potential therapeutic. One particular embodiment of the second aspect of the invention features transgenic animals engineered to develop amyloid-related pathologies (e.g., by the introduction of DNA effecting overexpression of β-amyloid). The potential therapeutic is administered (e.g. by intracerebral injection, or by system administration—oral or i.v.) to determine whether neuronal loss is reduced.

Also we have recognized that the entire β-amyloid protein itself, e.g., β amyloid residues 1–43 (SEQ ID NO: 70)

without the flanking APP sequences, is neurotoxic, and, indeed, polypeptides comprising residues 29–35 (SEQ ID NO: 71) alone of the β-amyloid protein are neurotoxic. This recognition is beneficial in the second aspect of the invention in which antagonists of such toxicity (tachykinins or other compounds) are identified as useful for treating disease characterized by neuronal accumulation of β-amyloid. Specifically, a neurotoxic polypeptide comprising at least residues 29–35 (SEQ ID NO: 71) (preferably 25–35 (SEQ ID NO: 1)) of the β-amyloid protein (without APP sequences flanking the full 43-residue β-amyloid protein) is administered to a sensitive cell in conjunction with the compound being tested as a toxicity antagonist to determine whether the compound reduces the effect of the neurotoxicity (e.g. reduces death) or reduces accumulation on the sensitive cell. This method has the advantage that the neurotoxin can be chemically synthesized rather than being produced by expression in an engineered cell, which, as a practical matter, is the method for producing larger derivatives of APP. See generally, PCT WO89/05138, hereby incorporated by reference. This aspect of the invention generally serves as a screening procedure for therapeutics related to diseases characterized by excessive neuronal deposits of β-amyloid.

It should be noted that neurotoxic β-amyloid related polypeptides can be neurotrophic at earlier stages of neuronal differentiation. The phenomenon of interest in the invention, however, is the effect of the neurotoxicity of such polypeptides to mature neurons.

Other features and advantages of the invention will be apparent from the following description of the preferred embodiments, and from the claims.

DESCRIPTION OF THE PREFERRED EMBODIMENT

The drawings will first briefly be described.

DRAWINGS

TACHYKININ AGONISTS

Tachykinin agonists useful in this invention can be identified by any of a number of techniques, specific examples of which are provided below. In general, tachykinin agonists are those polypeptides which are able to overcome or reduce the neurotoxic effect of β-amyloid related polypeptides. An example of such a neurotoxic effect is also provided below. The tachykinin agonists are able to reduce, or even prevent or reverse, the neurotoxic effects of neurotoxic β-amyloid related polypeptide. In particular, they are able to reduce the neurotoxic effects of the intact β1–40 (SEQ ID NO: 69) peptide or of a peptide that includes the 11 amino acid portion of the β-amyloid protein shown in FIG. 3, between amino acids 25 and 35 inclusive: GSNKGAIIGLM. (SEQ ID NO: 1) (As mentioned above, even the region 29–35 is adequate to generate neurotoxicity that can form the basis of an assay according to the invention.)

Potentially useful tachykinin agonists are those which have significant sequence similarity to either substance P, physalaemin, or neurokinin B. That is, they have either conservative amino acid substitutions at one or more positions. Preferably there are only one or two non-conservative substitutions in the proposed therapeutics, but the invention at its broadest level covers polypeptides with substantially more (e.g. 50%) substitutions to a proven tachykinin (e.g. substance P, physalaemin, or neurokinin B) only one or two of the amino acids of these compounds. As discussed above, useful agonists can be readily identified from such homologous compounds by standard techniques, examples of which are provided below.

Tachykinin agonists of this invention inhibit the toxic effects of β-amyloid-related proteins in the assay given below. These agonists are thought to interact at the receptor for substance P or the receptor for β-amyloid within the brain or with β amyloid itself; thus, tachykinin agonists which interact strongly at any one of these sites are particularly useful in this invention. Such agonists can again be identified by standard procedure by simply measuring their binding capacity for substance P receptors, for example, in a radioreceptor assay using substance P as a competitive binding agent for a substance P receptor.

There follows an example of a method by which the capacity of a potential tachykinin agonist to inhibit the deleterious effects of β amyloid can be measured. This example is provided to illustrate, not to limit the invention; those of ordinary skill in the art can readily determine other equivalent methods by which to measure the neurotoxic and neurotrophic effect of β-amyloid-related proteins, the reversal of such effect, or the inhibition of such effect by useful tachykinin agonists of this invention.

Figure 1A:
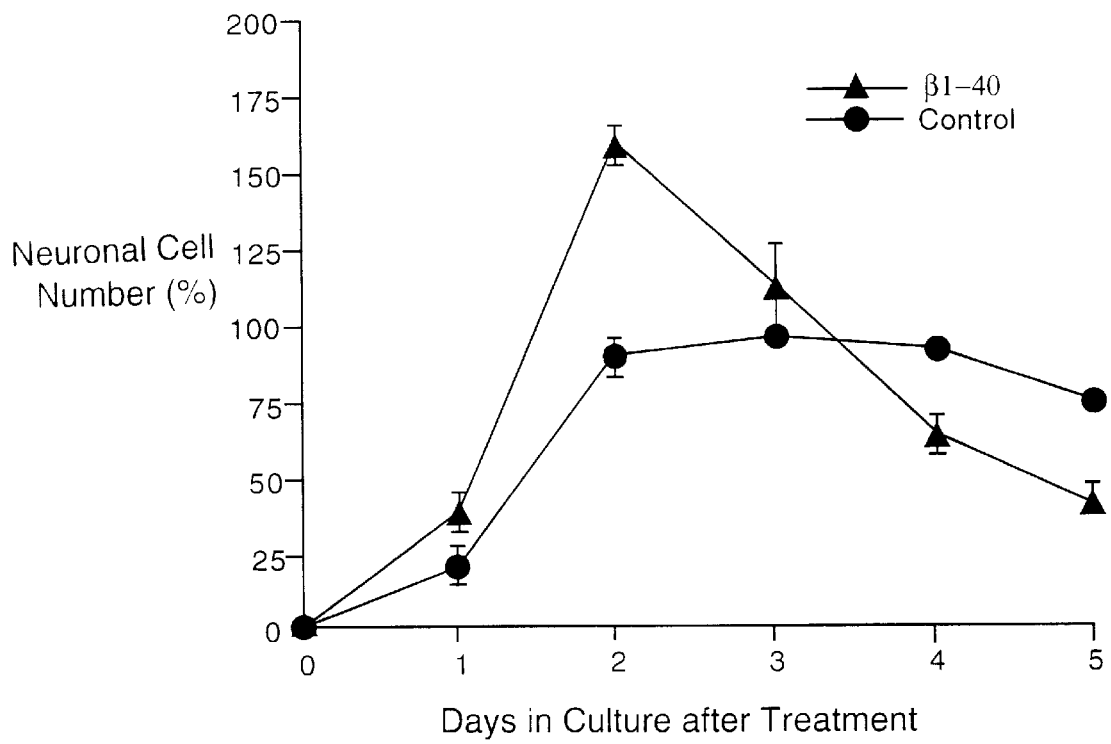
FIGS. 1A and 1B are graphical representations of the neurotrophic and neurotoxic effects of β-amyloid on hippocampal neurons.
Figure 3:
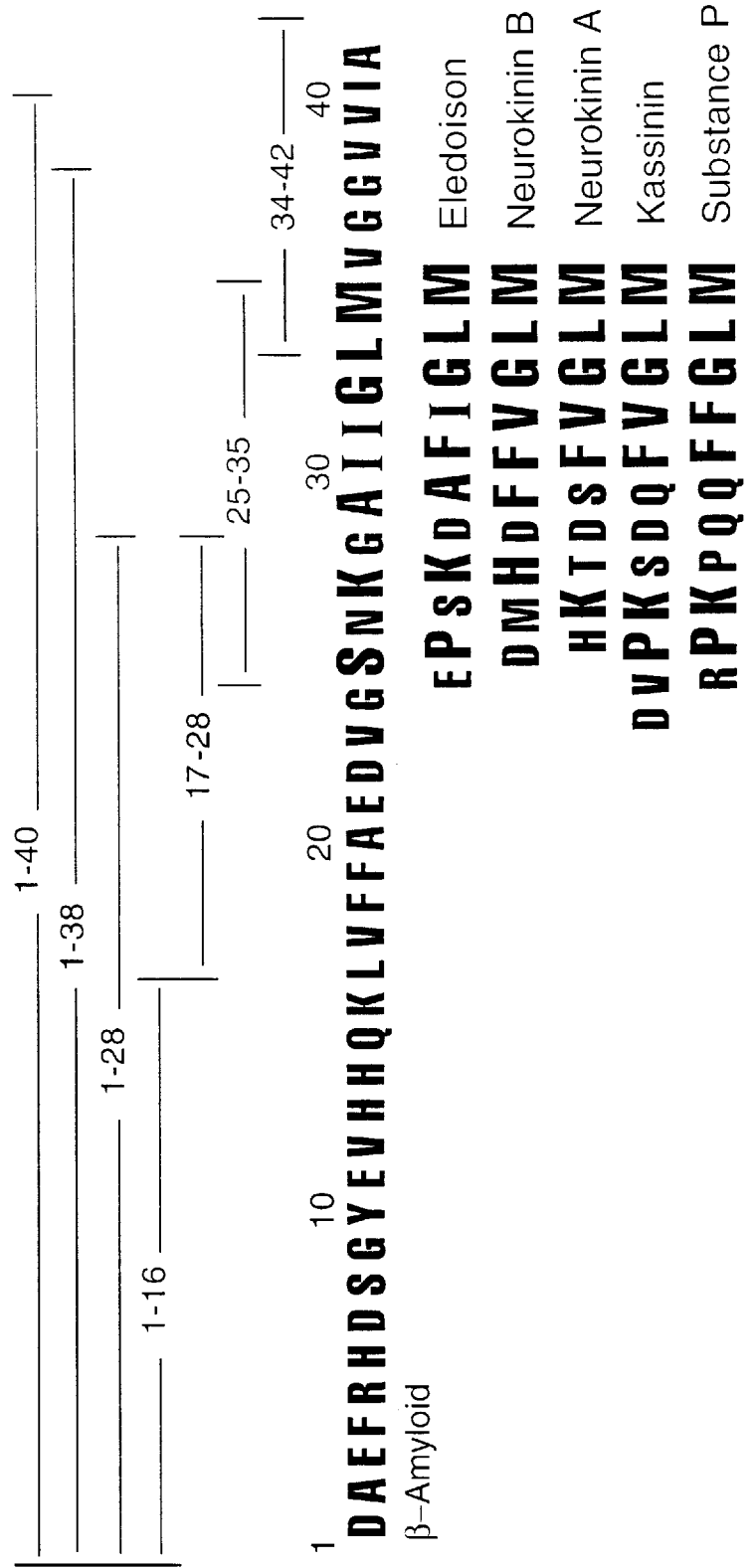
FIG. 3 is a representation of the amino acid sequence of β-amyloid and various tachykinin neuropeptides.

In this example, the polypeptide corresponding to the first 40 amino acids of β-amyloid (β1–40) (SEQ ID NO: 69) was synthesized, purified, and the primary sequence confirmed (see FIG. 3). Referring to FIG. 1, the effects of the β1–40 (SEQ ID NO: 69) polypeptide on hippocampal neurons was measured. As mentioned above, both neurotrophic and neurotoxic effects were observed, depending on the stage of neuronal development. In FIG. 1A, 20 μM β1–40 (SEQ ID NO: 69) was added to hippocampal neurons at plating to result in an early increase (0–2 days, neurotrophic) followed by a decrease (3–5 days, neurotoxic) in neuronal cell number. Thus, addition of β1–40 (SEQ ID NO: 69) to primary rat E18 hippocampal cultures at the time of subplating results in a significant increase in the number of pyramidal neurons during the first 2 days in culture. After 3 days in culture, however, there is a marked decline in neuronal cell number in cultures treated with β1–40 (SEQ ID NO: 69), and by 4–5 days the number of pyramidal neurons in β1–40 (SEQ ID NO: 69) treated cultures was significantly less than in control cultures.

Figure 1B:
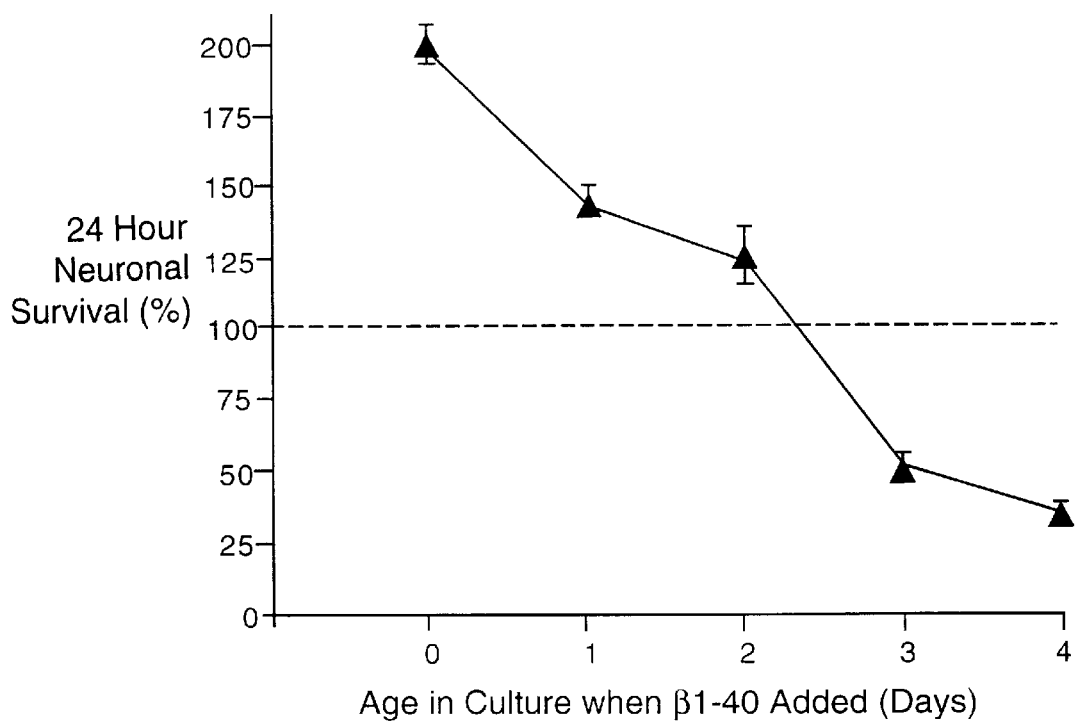

Referring to FIG. 1B, 20 μM β1–40 (SEQ ID NO: 69) was added to hippocampal neurons of different ages in culture, and the number of neurons determined 24 hours later. β1–40 (SEQ ID NO: 69) had a trophic effect on young neurons (values greater than 100% on days 0–2) and a toxic effect on older neurons (values less than 100% on days 3–5). The dashed line in the drawing indicates the transition from the trophic to toxic response. Thus, when β1–40 (SEQ ID NO: 69) is added at the time of plating (day 0) there is a significant increase in 24 hour neuronal survival relative to control values. This trophic effect progressively declines when β1–40 (SEQ ID NO: 69) is added during the next two days in culture. If β1–40 (SEQ ID NO: 69) is added to older cultures (3 days or later) there is an opposite effect, with a decline in 24 hour neuronal survival relative to controls. Control cultures remain viable and showed only a small change in neuronal survival using neurons up to 5 days old. These data show that β1–40 (SEQ ID NO: 69) is neurotrophic when added during the early period of neuronal differentiation (days 0–2) and neurotoxic to older more differentiated neurons, more similar to an adult state.

Figure 2:
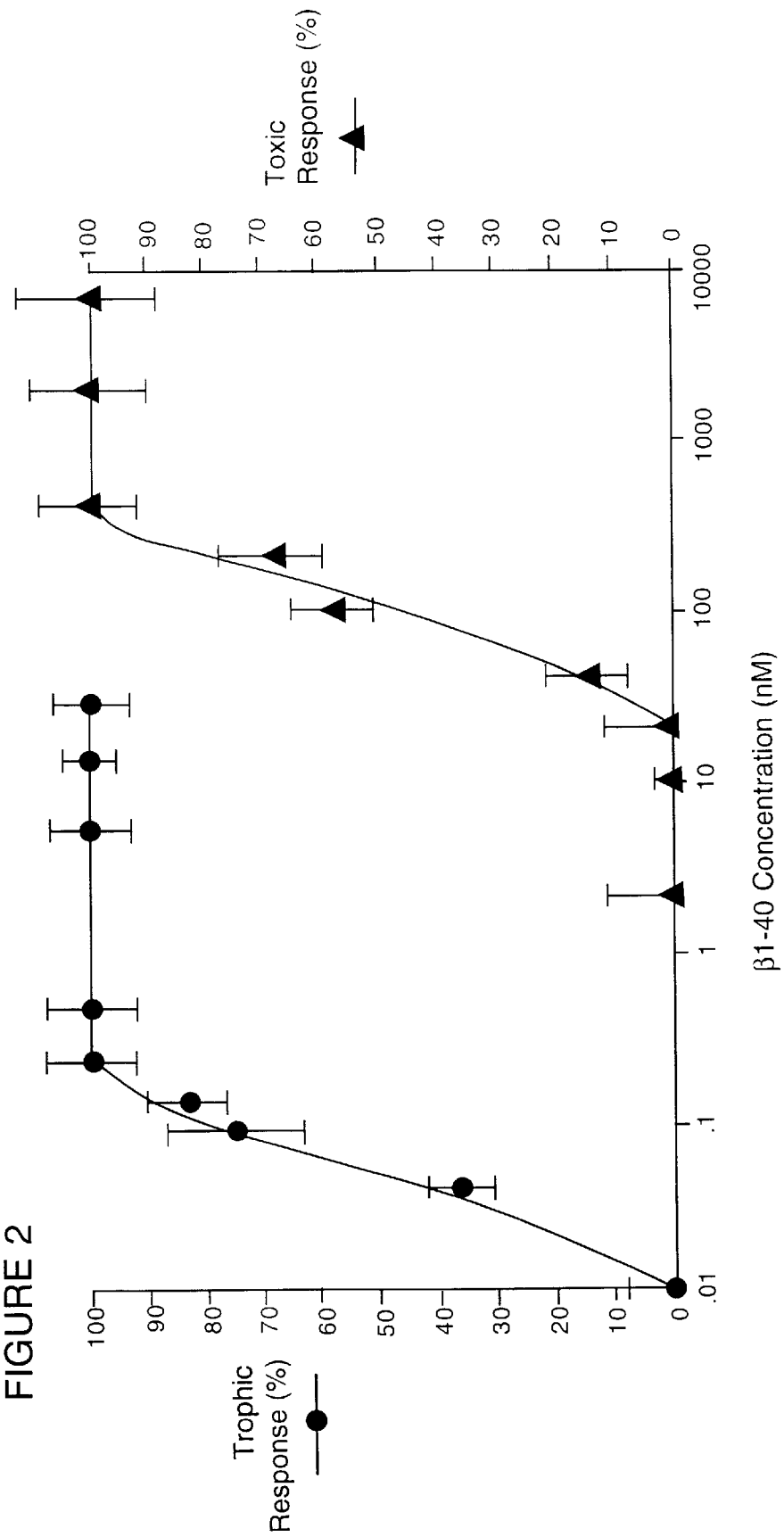
FIG. 2 is a graphical representation of the β-amyloid concentration dependence of the neurotrophic and neurotoxic responses.

Referring to FIG. 2, the neurotrophic and neurotoxic effects of β1–40 (SEQ ID NO: 69) was separately assayed by adding β1–40 (SEQ ID NO: 69) at day 0 and day 4, respectively, and determining 24 hour neuronal survival. The β1–40 (SEQ ID NO: 69) concentration dependency of the neurotrophic and neurotoxic effects is shown in FIG. 2. The neurotoxic response requires about 1000-fold higher concentration of β1–40 (SEQ ID NO: 69) than the neurotrophic response. The trophic response was determined by adding β1–40 (SEQ ID NO: 69) at the indicated concentrations to neurons at the time of plating (day 0); the toxic response was determined by adding β1–40 (SEQ ID NO: 69) to neurons at day 4 in culture. Values were normalized to the maximum β1–40 (SEQ ID NO: 69) -induced increase in neuronal cell number at day 0 (100% trophic response) and the maximum β1–40 (SEQ ID NO: 69) induced decrease in neuronal cell number at day 4 (100% toxic response). The trophic response was detected at very low levels of β1–40 (SEQ ID NO: 69) with an $EC_{50}$ of 0.06 nM. The toxic response required about 1000-fold higher concentrations of β1–40 (SEQ ID NO: 69); it was first detected at 40 nM, with an $EC_{50}$ of about 100 nM.

The APP domain responsible for neurotrophic and neurotoxic effects was determined by assaying overlapping peptides spanning the entire β-amyloid precursor sequence (see FIG. 3 and table 1). The figures in the table were determined by treating hippocampal neurons at the time of cell plating, or at 4 days in culture, with the indicated peptides to measure the early trophic or late toxic responses, respectively, one day later. Values were normalized to the mean day 1 response (trophic response) and day 5 decrease (toxic response) in neuronal cell number observed for β1–40 (SEQ ID NO: 69) (100% response). Peptide concentrations were at 20 μM except where indicated otherwise, and added directly to cell cultures. The values shown in the table are the mean ± the standard error of the mean using between 10 and 20 measurements for each peptide. The primary sequences of the designated β-amyloid sequences are shown in FIG. 3.

TABLE 1

| Peptide | % Trophic Response | % Toxic Response |
|---|---|---|
| β1-40 (SEQ ID NO: 69) | 100 ± 6 | 100 ± 7 |
| β1-38 (SEQ ID NO: 68) | 109 ± 10 | 97 ± 9 |
| β1-28 20μM | 0 ± 5 | 0 ± 6 |
| β-28 100 μM | 29 ± 10 | 55 ± 11 |
| β1-16 | 0 ± 8 | 0 ± 10 |
| β17-28 | 0 ± 4 | 0 ± 8 |
| β25-35 (SEQ ID NO: 1) | 100 ± 6 | 117 ± 12 |
| β32-42 | 0 ± 10 | 0 ± 7 |
| APP576-695 | 0 ± 4 | 0 ± 7 |
| Glucagon | 0 ± 3 | 0 ± 11 |
| Substance P | 16 ± 8 | 0 ± 7 |
| Physalaemin | 0 ± 4 | 0 ± 7 |
| Eledoisin | 0 ± 11 | 0 ± 6 |
| [D-Pro$^2$, D-Trp$^{7,9}$]] - substance P (SEQ ID NO: 2) | 125 ± 11 | 117 ± 13 |
| [D-Arq$^1$, D-Trp$^{7,9}$, Leu$^{11}$]-substance P (spantide) | | |

TABLE 1-continued

| Peptide | % Trophic Response | % Toxic Response |
|---|---|---|
| (SEQ ID NO: 3) | 120 ± 8 | 118 ± 10 |
| Spantide + Substance P | 0 ± 8 | 26 ± 7 |

β1–38 (SEQ ID NO: 68) elicited the same activity as β1–40 (SEQ ID NO: 69). β1–28 showed some early neurotrophic and late neurotoxic activity, but was much less potent than β1–40 (SEQ ID NO: 69) (Table 1). β1–16 and β17–28 showed no trophic or toxic activity at equimolar concentrations to β1–40 (SEQ ID NO: 69). β17–28 showed similar activity to β1–28 at higher concentrations. The β25–35 (SEQ ID NO: 1) peptide showed the same neurotrophic and neurotoxic activity as β1–40 (SEQ ID NO: 69). β34–42 as inactive. A peptide corresponding to the carboxyterminal 20 amino acids of the amyloid precursor protein (APP676–695) and glucagon, a 28 amino acid peptide possessing β-pleated sheet structure similar to that of β-amyloid, were both inactive. Thus, a sufficient portion of the functional domain of β-amyloid required for the toxic effects is contained in the β25–35 (SEQ ID NO: 1) sequence and even in the β29–35 (SEQ ID NO: 71) sequence. The dose response relationship shown in FIG. 2 for β1–40 (SEQ ID NO: 69) was also observed for β25–35 (SEQ ID NO: 1).

β25–35 (SEQ ID NO: 1) has 73% homology to eledoisin, including conservative changes, and 56% homology to the other tachykinins (FIG. 3). The region of greatest homology is in the carboxyterminal amino acids of the tachykinin sequence which is known to be required for high affinity tachykinin receptor binding and biological activity. Payan 40 Ann Rev. Med. 341, 1989.

Various tachykinins were tested for their effects on hippocampal neuronal survival. Exogenous substance P, eledoisin and physalaemin had no effect on early or late neuronal survival (Table 1). Tachykinin antagonists were also tested. The potent tachykinin antagonists [D-Pro$^2$, D-Trp$^{7,9}$]-substance P (SEQ ID NO: 2) and [D-Arg$^1$, D-Trp$^{7,9}$, Leu$^{11}$]-substance P (SEQ ID NO: 2) (spantide) (SEQ ID NO: 3) showed significant early neurotrophic and late neurotoxic effects which could be reversed by the addition of substance P (Table 1). The effects of tachykinin antagonists closely mimicked those of β1–40 (SEQ ID NO: 69) with respect to the time course and magnitude of changes in neuronal survival (Table 1).

Figure 4A:
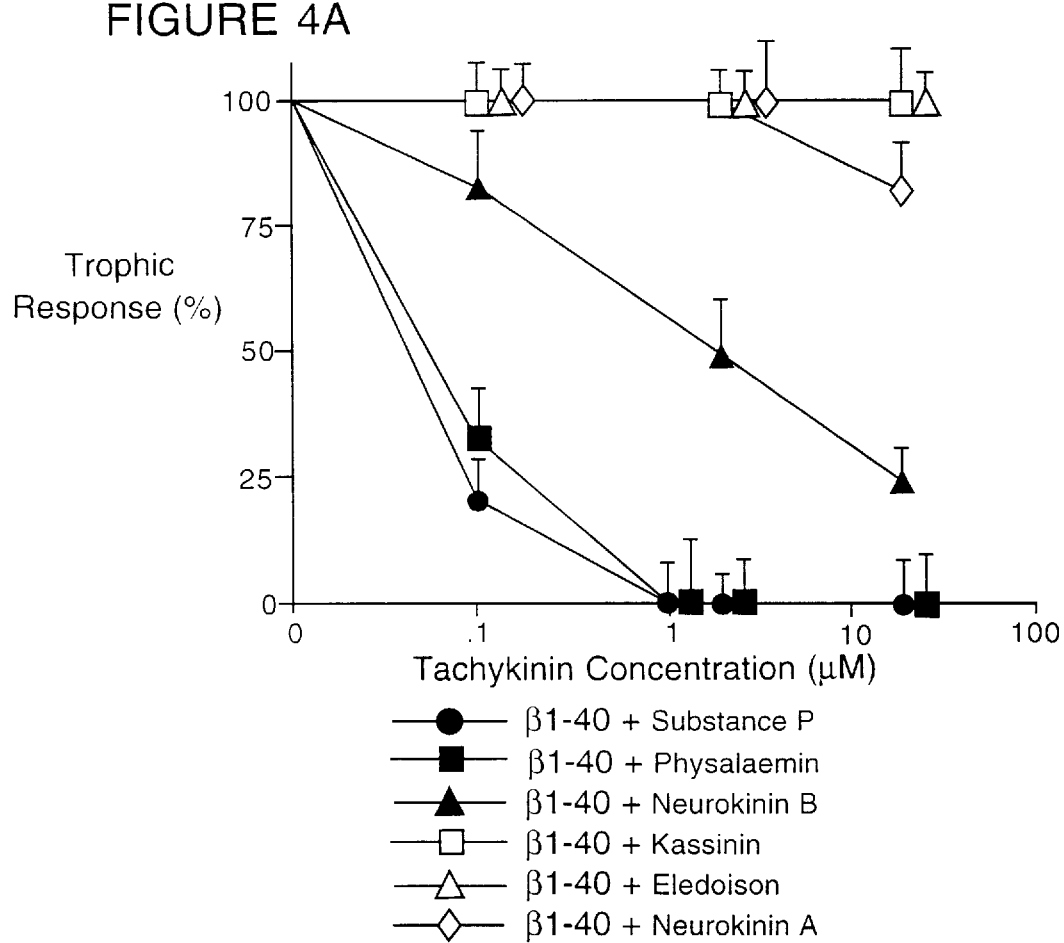
FIG. 4 is a graphical representation of the effect of tachykinins on the trophic and toxic responses to β-amyloid.
Figure 4B:
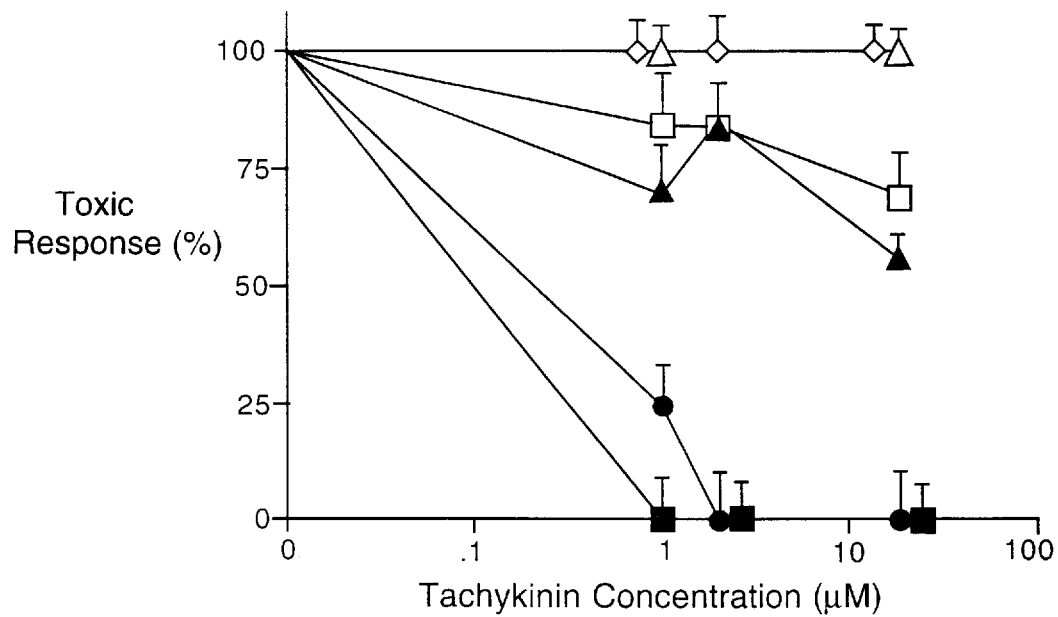

Since β-amyloid appears to have the same effects as tachykinin antagonists, the following experiment was performed to determine whether its activity could be reversed by tachykinin agonists. Tachykinin peptides were added along with β1–40 (SEQ ID NO: 69) to hippocampal neurons at the time of plating to assay the trophic effect. Similarly, the toxic effect was assayed by adding these compounds after 4 days to older neurons in culture. β1–40 (SEQ ID NO: 69) was maintained at 20 μM at the time of cell plating and the trophic response determined 1 day later. The results of such experiments are shown in FIGS. 4A and 4B.

Substance P and physalaemin almost completely reversed the early trophic and late toxic responses to β1–40 (SEQ ID NO: 69). Values were normalized to the mean day 0 trophic and day 4 toxic responses to β1–40 (SEQ ID NO: 69) alone (100%); substance P and physalaemin acted in a dose dependent manner. Neurokinin B partially reversed the activity of β1–40 (SEQ ID NO: 69), but was less potent than substance P and physalaemin. Neurokinin A, eledoisin and kassinin did not show significant effects in the concentration ranges tested. Thus, the effects of β-amyloid are selectively reversed by specific tachykinin neuropeptides.

An alternative method for identifying useful therapeutic that reverse the neurotoxicity of β amyloid involves intracerebral injection of β amyloid. Coadministration of the potential therapeutic compound is tested for its ability to prevent an intracerebral neurotoxic response to β amyloid alone or in combination with neurotrophic factors. For example, test animals such as rats or monkeys can be injected and, after treatment, can be autopsied using antibodies specific for Alzheimer's Disease, e.g. antibodies to Tau protein, A68 proteins, or ubiquitin.

Still another method for identifying useful therapeutic involves measuring the accumulation of a β amyloid peptide (as described above) on the surface of sensitive cell. Generally, the cells that are sensitive to β-amyloid toxicity, as mentioned above, can be used in the β amyloid "accumulation" assay. The measurement can be made by using antibodies to β amyloid or by staining with thioflavin S or congo red and measuring fluorescence, or green birefringence, respectively.

One cell line in particular that can be used in this aspect of the invention is PC-12, a cell line derived from a tumor (pheochromocytoma) of the adrenal medulla.

Still another method of identifying useful therapeutics involves the use of transgenic mammals that have been genetically engineered to overproduce β amyloid. See Quon et al. *Nature* (1991) 352:239–241 regarding such a transgenic mouse. See also Wirak et al. *Science* (1991) 253:323–325; and Marx, *Science* (1991) 253:266–267. Neuronal death is measured as a control, and the potential therapeutic is administered. A determination (e.g. autopsy and staining) is then made on the mouse's neurons to ascertain amelioration of the neuronal death.

Other tachykinin agonists suitable for use in the invention include fragments of Substance P which counteract the neurotoxicity of β amyloid peptides in the above-described assays.

As one specific example, the Substance P fragment comprising amino acid residues 1–7 ("Substance P (1–7)") is suitable for use in the invention. The sequence of Substance P (1–7) is RPKPQQF (SEQ ID NO: 4). Advantageously, Substance P (1–7) (SEQ ID NO: 4) has substantial therapeutic efficacy, but it has less biological activity than Substance P on peripheral organs (i.e., organs outside the central nervous system), thereby reducing potential side effects to patients.

Without limiting the scope of the invention I illustrate it with the following additional specific fragments of Substance P: Sub P (6–11)—QFFGLM (SEQ ID NO: 5); and Sub P (7–11)—FFGLM (SEQ ID NO: 6); Sub P (1–4)—RPKP (SEQ ID NO: 7), Sub P (5–11)—QQFFGLM (SEQ ID NO: 8). Substance P (2–11)—PKPQQFFGLM (SEQ ID NO:9); Substance P (4–11)—PQQFFGLM (SEQ ID NO: 10); and Substance P (1–9)13 RPKPQQFFG (SEQ ID NO: 11).

Still other tachykinin antagonists useful in the invention are tachykinins in which amino acid substitutions have been made. For example Substance P may be modified by substituting Tyr for Phe in position 7 (SEQ ID NO: 12), or methionine for Gly in position 11 (SEQ ID NO: 13) or nor-leucine for Gly in position 11 (SEQ ID NO: 14), or Ile for Phe at position 8 (SEQ ID NO: 15). Other analogues with relevant activity are $Arg^1 \rightarrow pGlu$ (SEQ ID NO: 16); $Phe^7 \rightarrow Met$ (SEQ ID NO: 17).

Substance P is somewhat stable on passage through the circulatory system. Certain active analogs, e.g., Pro in place of Arg (1) (SEQ ID NO: 18), or Lys (3) (SEQ ID NO: 19) reduce enzymatic degradation or Substance P and retain activity. Similarly, Substance P analogs with one or more of the following substitutions ($Gln^5 \rightarrow Glu$ (SEQ ID NO: 25), $Phe^8 \rightarrow MePhe$ (SEQ ID NO: 26), and $Gly^9 \rightarrow MeGly$) (SEQ ID NO: 27) are more resistant to degradation.

Other analogues include alkyl (e.g., methyl, ethyl, or propyl esters of Substance P (i.e., the terminal Met—$NH_2$ is Met—$OCH_3$ or Met—$OCH_2CH_3$ or Met—$O$—$CH_2CH_2CH_3$) or the free acid of substance P in which the terminal Met—$NH_2$ is (Met—OOH). Still other analogs of Substance P are those with the following substitutions: $Ala^9$ (SEQ ID NO: 20) $D-Ala^9$ (SEQ ID NO: 21) $Sar^9$ (SEQ ID NO: 22) $Pro^9$ (SEQ ID NO: 23) or $D-Pro^9$; (SEQ ID NO: 24) $MeLeu^{10}$ (SEQ ID NO: 66) or $Pro^{10}$; (SEQ ID NO: 62); $MeMet^{11}$ (SEQ ID NO: 67) or $Pro^{11}$ (SEQ ID NO: 64).

Still other useful analogs are cyclic peptides in which cysteine or homocysteine is introduced particularly at 5, 9 and 5, 10 and 5, 11 positions in two locations to permit disulfide bridge cyclization. Useful compounds include $[Cys^{5,9}]SP$ (SEQ ID NO: 28); $[Hcy^{5,9}]SP$; (SEQ ID NO: 29) $[D-Cys^5, Hcy^{10}]SP$ (SEQ ID NO: 30); $[Cys^{5,11}]SP$ (SEQ ID NO: 31); $[Hcy^{5,11}]SP$ (SEQ ID NO: 32).

Other useful cyclic analogs of Substance P are given below:

$[D-Cys^5, Cys^8]SP$ (SEQ ID NO: 33); $[D-Cys^5, Cys^7]SP$ (SEQ ID NO: 34); $[D-Cys^3, Cys^6]SP$ (SEQ ID NO: 35); $[Cys^{3,6}]SP$ (SEQ ID NO: 36); $[CyS^{3,6}, Tyr^8]SP$ (SEQ ID NO: 37); $[Cys^{3,6}, Val^8]SP$ (SEQ ID NO: 38); $[Cys^{3,6}, Tyr^8, Ala^9]SP$ (SEQ ID NO: 39); $[Cys^{3,6}, Tyr^8, Pro^9]SP$ (SEQ ID NO: 40); $[Cys^{3,6}, Tyr^8, Pro^{10}]SP$ (SEQ ID NO: 41).

Other useful analogs of Neurokinin B (NKB) or Substance P are:

$[Cys^{7,5}]NKB$ (SEQ ID NO: 42); $[Me—Val^7]NKB$ (SEQ ID NO: 43); $[Pro^7]NKB$ (SEQ ID NO: 44); $[pGlu^6, Pro^9]SP(6-11)^+$ (SEQ ID NO: 45); $[pGlu^5, MePhe^8]$-Sub P (5–11)]=GFFMePheLM (SEQ ID NO: 46)

$[Nle^{11}]$-SP (7–11)—FFGLNle (SEQ ID NO: 47)

$[Tyr^7]$-SP (7–11)—YFGLM (SEQ ID NO: 48)

$[Eth^{11}]$-SP (7–11)—FFGLEth (SEQ ID NO: 49).

Finally, the following Substance P analogs are suitable for use in the invention:

$[pGlu^5, MePhe^8, Sar^9]$-Sub P (5–11) (SEQ ID NO: 50)

$[Asp^{5,6}, MePhe^8]$ Sub P (5–11) (Senktide Analog) (SEQ ID NO: 51)

$[N-Acetyl-Arg^6, MePhe^8]$-Sub P (6–11) (Senktide) (SEQ ID NO: 52)

$[pGlu^6, Pro^9]$-Sub P (6–11) (Septide) (SEQ ID NO: 53)

$[p-Chloro-Phe^{7,8}]$-Sub P (SEQ ID NO: 54)

$[Sar^9, Met (O_2)^{11}]$-Sub P (SEQ ID NO: 55)

$[D-Ala^4]$-Sub P (4–11)] (SEQ ID NO: 56).

Still further analogs are those described in Scandrett, U.S. Pat. No. 3,862,114, which is hereby incorporated by reference.

EXAMPLES

Substance P and various analogs were tested for therapeutic potency. Specifically, as a control, primary hippocampal neurons were incubated with the β-amyloid peptide (β1–40) (SEQ ID NO: 69) as generally described above. The control showed 53% neuronal loss after 24 hours of incubation. In the presence of 10 μg/ml of Substance P, the toxicity of (β1–40) (SEQ ID NO: 69) was completely blocked. The substance P analogs were also added to separate cultures at a concentration of 10 μg/ml. The ability of the analogs to block neuronal toxicity is expressed below:

| Peptide | Therapeutic Efficacy (%) |
|---|---|
| Sub P | 100 |
| Sub P (1–7) | 82 |
| Sub P (6–11) (SEQ ID NO: 5) | 65 |
| Sub P (7–11) (SEQ ID NO: 6) | 41 |
| [Nle$^{11}$]-Sub P (SEQ ID NO: 14) | 77 |
| Sub P, Methyl Ester | 71 |
| Sub P, Free Acid | 53 |
| [Cys$^{3,6}$, Tyr$^{8}$, Pro$^{9}$]-Sub P (SEQ ID NO:40) | 53 |
| [pGlu$^{5}$, Me-Phe$^{8}$, Sar$^{9}$]-Sub P (5–11) (SEQ ID NO: 50) | 41 |
| [Succinyl-Asp$^{6}$, Me-Phe$^{8}$]-Sub P (6–11) (Senktide) (SEQ ID NO: 52) | 47 |

The above described analogs generally can be purchased (e.g., from Peninsula Lab, Inc., San Carlos, Calif. and Bachem Fine Chemicals, Torrence Calif.) and therapeutic compositions can be prepared by standard techniques for purification and formulation into a pharmaceutically acceptable vehicle. Those compounds which are not readily available commercially can be prepared by solid phase synthesis: Merrifield, *J. Am. Chem. Soc.* 85:2149 (1963). Other synthetic techniques are disclosed in Chipkin et al., *Arch. Int. Pharmacodyn.* "SP and Analogs" 240:193–202 (1979); Eison et al., *Science* (1982) 188–190 "Substance P Analog, DiMe-C7: Evidence For Stability in Rat Brain and Prolonged Central Action"; Bar-Shavitt et al., *Biochem. Biophys. Res. Com.* 94:1445–1451 (1980); Lavielle et al., *Biochem. Pharm.* 37:41–49 (1988).

In as much as it is clearly possible to inhibit binding between Substance P and its receptor (the NK1 receptor) using nonpeptides [see Snider et al. *Science* 251:435–437 (1991)], nonpeptide agonists of Substance P are also within the scope of this invention.

Use

Tachykinin agonists of this invention are useful for treatment of diseases characterized by accumulations of β-amyloid within a central nervous system. Such diseases include Alzheimer's disease, Down's syndrome, and the syndromes of hereditary cerebral hemorrhage with amyloidosis and non-inherited congophilic angiopathy with cerebral hemorrhage. Patients who are at risk or who may be affected by such diseases can be generally identified by procedures well known to those of ordinary skill in the art, including external manifestations of such diseases, such as declined mental efficiency and focal neurological deficits. They may also be characterized by detection of β-amyloid accumulation as described by Joachiun et al. 341 Nature 226, 1989. Once characterized, these patients can be treated by administering a tachykinin antagonist of this invention in an amount sufficient to reduce symptoms of the disease, or to inhibit progress of the disease. The amount of agonist to be administered will vary dependent upon the agonist, and can be determined by standard procedures. For any particular agonists, it is expected that a useful dose will be in the range of one nanomolar to one micromolar agonist, administered with a physiologically acceptable carrier either systemically or directly to the central nervous system. The agonist may be administered orally or by intravenous, subcutaneous or intramuscular injection directly into the patients' tissues. The peptides may also be modified to enhance their absorption directly into the body, and thus may be administered topically. The agonist may be administered directly into the brain by an indwelling catheter or pump device which delivers the agonist into the cerebral ventricles or intrathecal spaces.

One specific drug delivery system relies on redox interconversion of dihydropyridine and a pyridinium salt carrier. See Sodor et al. Science, 214:1370 et seq. (1981). That system describes attaching the pyridinium salt carrier by a dehydration reaction to the amino terminus of the peptide to be delivered. The carboxyl terminus is protected by methanol condensation with the free acid to produce the methyl ester.

Following intravenous injection, the compound will cross the blood-brain barrier and will be distributed throughout the body, including the brain. Drug removal occurs as the dihydropyridine carrier is oxizided to the original charged pyridinium quaternary salt, which is eliminated. Enzymatic cleavage of the carrier drug combination traps the drug in the central nervous system, resulting in sustained delivery of substance P to neurons.

Substance P itself is known to cross the blood-brain barrier, (See, e.g., Banks et al. Res. Bul., 15:287–292 (1985)) and therefore may be administered systemically. It is also known to be somewhat stable to protease degradations. In general, less charged substance P analogs (such as [Nle"]-Sub P and Sub P-methyl ester therefore, also cross the blood-brain barrier. Such compounds can also be administered systemically, e.g., orally, intravenously, or intramuscularly. In general, the ability of therapeutic Substance P fragments and derivatives to cross the blood-brain barrier can be measured by the method described by Banks et al. Those with suitable ability to cross can be administered systemically, preferably orally.

Other embodiments are within the following claims.

I claim:

1. A method of screening candidate compounds to identify a compound capable of inhibiting a neurotoxin, said method comprising the steps of:
  (a) providing a cell, said cell being a primary neuron, a neuronal cell or a cell developmentally derived from neuronal tissue;
  (b) contacting said cell with a neurotoxin and a candidate compound, said neurotoxin being β1–38 (SEQ ID NO: 68), β1–40 (SEQ ID NO: 69), β1–43 (SEQ ID NO: 70), β29–35 (SEQ ID NO: 71), or β25–35 (SEQ ID NO:1); and
  (c) determining the neurotoxic effect of said neurotoxin on said cell, wherein a decrease in said neurotoxic effect in the presence of said candidate compound compared to the neurotoxic effect in the absence of said candidate compound indicates that said candidate compound inhibits said neurotoxin.

2. A method for identifying a compound for antagonizing neuronal accumulation of β-amyloid on a cell surface, said method comprising the steps of:
  a) providing a candidate compound to be tested;
  b) providing a cell, said cell being a primary neuron, a neuronal cell or a cell developmentally derived from neuronal tissue;
  c) contacting said cell with a neurotoxin and said candidate compound, wherein said neurotoxin is β1–38 (SEQ ID NO: 68), β1–40 (SEQ ID NO: 69), β1–43

(SEQ ID NO: 70), β29–35 (SEQ ID NO: 71), or β25–35 (SEQ ID NO: 1), wherein said β-amyloid or β-amyloid-related polypeptide accumulates on the surface said cell; and d) determining whether said compound reduces the accumulation of said β1–38 (SEQ ID NO: 68), β1–40 (SEQ ID NO: 69), β1–43 (SEQ ID NO: 70), β29–35 (SEQ ID NO: 71), or β25–35 (SEQ ID NO: 1) on said cells; wherein a reduction of accumulation in the presence of said compound is indicative of said compound being useful for antagonizing neuronal accumulation of β-amyloid.

3. The method of claim 2 wherein said accumulation is determined by immunohistochemical staining.

4. The method of claim 2 wherein said accumulation is determined by binding of a radiolabelled β-amyloid polypeptide.

5. The method of claim 2 wherein said accumulation is measured by indirect staining.

6. The method of claim 2 or claim 1 wherein said cells are the PC-12 cell line.

* * * * *

SEQUENCE LISTING ( 1 ) GENERAL INFORMATION:

( i i i ) NUMBER OF SEQUENCES: 77

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

Gly Ser Gln Lys Gly Ala Ile Ile Gly Leu Met
 1               5                       10

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
        ( B ) LOCATION: 2...2
        ( D ) OTHER INFORMATION: where Xaa at position 2 is D-Pro ( B ) LOCATION: 7...7
        ( D ) OTHER INFORMATION: where Xaa at position 7 is D-Drp ( B ) LOCATION: 9...9
        ( D ) OTHER INFORMATION: where Xaa at position 9 is D-Trp ( x i ) SEQUENCE DESCRIPTION: SEQ ID NO:2:

Arg Xaa Lys Pro Gln Gln Xaa Phe Xaa Leu Met
 1               5                       10

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
        ( B ) LOCATION: 1...1
        ( D ) OTHER INFORMATION: where Xaa at position 1 is D-Arg ( B ) LOCATION: 7...7
        ( D ) OTHER INFORMATION: where Xaa at position 7 is D-Trp ( B ) LOCATION: 9...9
        ( D ) OTHER INFORMATION: where Xaa at position 9 is D-Trp ( x i ) SEQUENCE DESCRIPTION: SEQ ID NO:3:

Xaa Pro Lys Pro Gln Gln Xaa Phe Xaa Leu Leu
 1               5                       10

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Arg Pro Lys Pro Gln Gln Phe
 1               5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear (i i) MOLECULE TYPE: protein (x i) SEQUENCE DESCRIPTION: SEQ ID NO:5:

Gln Phe Phe Gly Leu Met
1               5

(2) INFORMATION FOR SEQ ID NO:6:

(i) SEQUENCE CHARACTERISTICS:
        (A) LENGTH: 5 amino acids
        (B) TYPE: amino acid
        (D) TOPOLOGY: linear (i i) MOLECULE TYPE: protein (x i) SEQUENCE DESCRIPTION: SEQ ID NO:6:

Phe Phe Gly Leu Met
1             5

(2) INFORMATION FOR SEQ ID NO:7:

(i) SEQUENCE CHARACTERISTICS:
        (A) LENGTH: 4 amino acids
        (B) TYPE: amino acid
        (D) TOPOLOGY: linear (i i) MOLECULE TYPE: protein (x i) SEQUENCE DESCRIPTION: SEQ ID NO:7:

Arg Pro Lys Pro
1

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: linear (i i) MOLECULE TYPE: protein (x i) SEQUENCE DESCRIPTION: SEQ ID NO:8:

Gln Gln Phe Phe Gly Leu Met
1               5

(2) INFORMATION FOR SEQ ID NO:9:

(i) SEQUENCE CHARACTERISTICS:
        (A) LENGTH: 10 amino acids
        (B) TYPE: amino acid
        (D) TOPOLOGY: linear (i i) MOLECULE TYPE: protein (x i) SEQUENCE DESCRIPTION: SEQ ID NO:9:

Pro Lys Pro Gln Gln Phe Phe Gly Leu Met
1               5                   10

(2) INFORMATION FOR SEQ ID NO:10:

(i) SEQUENCE CHARACTERISTICS:
        (A) LENGTH: 8 amino acids
        (B) TYPE: amino acid
        (D) TOPOLOGY: linear (i i) MOLECULE TYPE: protein (x i) SEQUENCE DESCRIPTION: SEQ ID NO:10:

Pro Gln Gln Phe Phe Gly Leu Met
1               5

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:11:

Arg Pro Lys Pro Gln Gln Phe Phe Gly
1               5

(2) INFORMATION FOR SEQ ID NO:12:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:12:

Arg Pro Lys Pro Gln Gln Tyr Phe Gly Leu Met
1               5                   10

(2) INFORMATION FOR SEQ ID NO:13:

(i) SEQUENCE CHARACTERISTICS:
        (A) LENGTH: 11 amino acids
        (B) TYPE: amino acid
        (D) TOPOLOGY: linear (ii) MOLECULE TYPE: protein (ix) FEATURE:
        (B) LOCATION: 11...11
        (D) OTHER INFORMATION: where Xaa at position 11 is ethionine (xi) SEQUENCE DESCRIPTION: SEQ ID NO:13:

Arg Pro Lys Pro Gln Gln Phe Phe Gly Leu Xaa
1               5                   10

(2) INFORMATION FOR SEQ ID NO:14:

(i) SEQUENCE CHARACTERISTICS:
        (A) LENGTH: 11 amino acids
        (B) TYPE: amino acid
        (D) TOPOLOGY: linear (ii) MOLECULE TYPE: protein (ix) FEATURE:
        (B) LOCATION: 11...11
        (D) OTHER INFORMATION: where Xaa at position 11 is Nle (xi) SEQUENCE DESCRIPTION: SEQ ID NO:14:

Arg Pro Lys Pro Gln Gln Phe Phe Gly Leu Xaa
1               5                   10

(2) INFORMATION FOR SEQ ID NO:15:

(i) SEQUENCE CHARACTERISTICS:
        (A) LENGTH: 11 amino acids
        (B) TYPE: amino acid
        (D) TOPOLOGY: linear (i i) MOLECULE TYPE: protein (x i) SEQUENCE DESCRIPTION: SEQ ID NO:15:

Arg Pro Lys Pro Gln Gln Phe Ile Gly Leu Met
1               5                   10

(2) INFORMATION FOR SEQ ID NO:16:

(i) SEQUENCE CHARACTERISTICS:
        (A) LENGTH: 11 amino acids
        (B) TYPE: amino acid
        (D) TOPOLOGY: linear (i i) MOLECULE TYPE: protein (i x) FEATURE:
        (B) LOCATION: 1...1
        (D) OTHER INFORMATION: where Xaa at position 1 is ethionine (x i) SEQUENCE DESCRIPTION: SEQ ID NO:16:

Xaa Pro Lys Pro Gln Gln Phe Phe Gly Leu Met
1               5                   10

(2) INFORMATION FOR SEQ ID NO:17:

(i) SEQUENCE CHARACTERISTICS:
        (A) LENGTH: 11 amino acids
        (B) TYPE: amino acid
        (D) TOPOLOGY: linear (i i) MOLECULE TYPE: protein (x i) SEQUENCE DESCRIPTION: SEQ ID NO:17:

Arg Pro Lys Pro Gln Gln Met Phe Gly Leu Met
1               5                   10

(2) INFORMATION FOR SEQ ID NO:18:

(i) SEQUENCE CHARACTERISTICS:
        (A) LENGTH: 11 amino acids
        (B) TYPE: amino acid
        (D) TOPOLOGY: linear (i i) MOLECULE TYPE: protein (x i) SEQUENCE DESCRIPTION: SEQ ID NO:18:

Pro Pro Lys Pro Gln Gln Phe Phe Gly Leu Met
1               5                   10

(2) INFORMATION FOR SEQ ID NO:19:

(i) SEQUENCE CHARACTERISTICS:
        (A) LENGTH: 11 amino acids
        (B) TYPE: amino acid
        (D) TOPOLOGY: linear (i i) MOLECULE TYPE: protein (x i) SEQUENCE DESCRIPTION: SEQ ID NO:19:

Arg Pro Pro Pro Gln Gln Phe Phe Gly Leu Met
1               5                   10

(2) INFORMATION FOR SEQ ID NO:20:

(i) SEQUENCE CHARACTERISTICS:
        (A) LENGTH: 11 amino acids
        (B) TYPE: amino acid
        (D) TOPOLOGY: linear (i i) MOLECULE TYPE: protein ( x i ) SEQUENCE DESCRIPTION: SEQ ID NO:20:

Arg Pro Lys Pro Gln Gln Phe Phe Ala Leu Met
1               5                       10

( 2 ) INFORMATION FOR SEQ ID NO:21:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( i x ) FEATURE:
    ( B ) LOCATION: 9...9
    ( D ) OTHER INFORMATION: where Xaa at position 9 is D-Ala ( x i ) SEQUENCE DESCRIPTION: SEQ ID NO:21:

Arg Pro Lys Pro Gln Gln Phe Phe Xaa Leu Met
1               5                       10

( 2 ) INFORMATION FOR SEQ ID NO:22:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( i x ) FEATURE:
    ( B ) LOCATION: 9...9
    ( D ) OTHER INFORMATION: where Xaa at position 9 is Sar ( x i ) SEQUENCE DESCRIPTION: SEQ ID NO:22:

Arg Pro Lys Pro Gln Gln Phe Phe Xaa Leu Met
1               5                       10

( 2 ) INFORMATION FOR SEQ ID NO:23:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( x i ) SEQUENCE DESCRIPTION: SEQ ID NO:23:

Arg Pro Lys Pro Gln Gln Phe Phe Pro Leu Met
1               5                       10

( 2 ) INFORMATION FOR SEQ ID NO:24:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( i x ) FEATURE:
    ( B ) LOCATION: 9...9
    ( D ) OTHER INFORMATION: where Xaa at position 9 is D-Pro ( x i ) SEQUENCE DESCRIPTION: SEQ ID NO:24:

Arg Pro Lys Pro Gln Gln Phe Phe Xaa Leu Met
1               5                       10

( 2 ) INFORMATION FOR SEQ ID NO:25:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( x i ) SEQUENCE DESCRIPTION: SEQ ID NO:25:

Arg Pro Lys Pro Glu Gln Phe Phe Gly Leu Met
 1               5                       10

( 2 ) INFORMATION FOR SEQ ID NO:26:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
        ( B ) LOCATION: 8...8
        ( D ) OTHER INFORMATION: where Xaa at position 8 is Me-Phe ( x i ) SEQUENCE DESCRIPTION: SEQ ID NO:26:

Arg Pro Lys Pro Gln Gln Phe Xaa Gly Leu Met
 1               5                       10

( 2 ) INFORMATION FOR SEQ ID NO:27:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
        ( B ) LOCATION: 9...9
        ( D ) OTHER INFORMATION: where Xaa at position 9 is Me-Gly ( x i ) SEQUENCE DESCRIPTION: SEQ ID NO:27:

Arg Pro Lys Pro Gln Gln Phe Phe Xaa Leu Met
 1               5                       10

( 2 ) INFORMATION FOR SEQ ID NO:28:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

Arg Pro Lys Pro Cys Gln Phe Phe Cys Leu Met
 1               5                       10

( 2 ) INFORMATION FOR SEQ ID NO:29:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
        ( B ) LOCATION: 5...5
        ( D ) OTHER INFORMATION: where Xaa at position 5 is homocysteine
        ( B ) LOCATION: 9...9

( D ) OTHER INFORMATION: where Xaa at position 9 is homocysteine ( x i ) SEQUENCE DESCRIPTION: SEQ ID NO:29:

Arg Pro Lys Pro Xaa Gln Phe Phe Xaa Leu Met
1               5                   10

( 2 ) INFORMATION FOR SEQ ID NO:30:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
        ( B ) LOCATION: 5...5
        ( D ) OTHER INFORMATION: where Xaa at position 5 is homocysteine
        ( B ) LOCATION: 10...10
        ( D ) OTHER INFORMATION: where Xaa at position 10 is
            homocysteine ( x i ) SEQUENCE DESCRIPTION: SEQ ID NO:30:

Arg Pro Lys Pro Xaa Gln Phe Phe Gly Xaa Met
1               5                   10

( 2 ) INFORMATION FOR SEQ ID NO:31:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

Arg Pro Lys Pro Cys Gln Phe Phe Gly Leu Cys
1               5                   10

( 2 ) INFORMATION FOR SEQ ID NO:32:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
        ( B ) LOCATION: 5...5
        ( D ) OTHER INFORMATION: where Xaa at position 5 is homocysteine
        ( B ) LOCATION: 11...11
        ( D ) OTHER INFORMATION: where Xaa at position 11 is
            homocysteine ( x i ) SEQUENCE DESCRIPTION: SEQ ID NO:32:

Arg Pro Lys Pro Xaa Gln Phe Phe Gly Leu Xaa
1               5                   10

( 2 ) INFORMATION FOR SEQ ID NO:33:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
        ( B ) LOCATION: 5...5
        ( D ) OTHER INFORMATION: where Xaa at position 5 is D-Cys ( x i ) SEQUENCE DESCRIPTION: SEQ ID NO:33:

Arg Pro Lys Pro Xaa Gln Phe Cys Gly Leu Met
1               5                   10

( 2 ) INFORMATION FOR SEQ ID NO:34:

( i ) SEQUENCE CHARACTERISTICS:
( A ) LENGTH: 11 amino acids
( B ) TYPE: amino acid
( D ) TOPOLOGY: linear ( i i ) MOLECULE TYPE: protein ( i x ) FEATURE:
( B ) LOCATION: 5...5
( D ) OTHER INFORMATION: where Xaa at position 5 is D-Cys ( x i ) SEQUENCE DESCRIPTION: SEQ ID NO:34:

Arg Pro Lys Pro Xaa Gln Cys Phe Gly Leu Met
1               5                   10

( 2 ) INFORMATION FOR SEQ ID NO:35:

( i ) SEQUENCE CHARACTERISTICS:
( A ) LENGTH: 11 amino acids
( B ) TYPE: amino acid
( D ) TOPOLOGY: linear ( i i ) MOLECULE TYPE: protein ( i x ) FEATURE:
( B ) LOCATION: 3...3
( D ) OTHER INFORMATION: where Xaa at position 3 is D-Cys ( x i ) SEQUENCE DESCRIPTION: SEQ ID NO:35:

Arg Pro Xaa Pro Gln Cys Phe Phe Gly Leu Met
1               5                   10

( 2 ) INFORMATION FOR SEQ ID NO:36:

( i ) SEQUENCE CHARACTERISTICS:
( A ) LENGTH: 11 amino acids
( B ) TYPE: amino acid
( D ) TOPOLOGY: linear ( i i ) MOLECULE TYPE: protein ( x i ) SEQUENCE DESCRIPTION: SEQ ID NO:36:

Arg Pro Cys Pro Gln Cys Phe Phe Gly Leu Met
1               5                   10

( 2 ) INFORMATION FOR SEQ ID NO:37:

( i ) SEQUENCE CHARACTERISTICS:
( A ) LENGTH: 11 amino acids
( B ) TYPE: amino acid
( D ) TOPOLOGY: linear ( i i ) MOLECULE TYPE: protein ( x i ) SEQUENCE DESCRIPTION: SEQ ID NO:37:

Arg Pro Cys Pro Gln Cys Phe Tyr Gly Leu Met
1               5                   10

( 2 ) INFORMATION FOR SEQ ID NO:38:

( i ) SEQUENCE CHARACTERISTICS:
( A ) LENGTH: 11 amino acids
( B ) TYPE: amino acid
( D ) TOPOLOGY: linear (ii) MOLECULE TYPE: protein (xi) SEQUENCE DESCRIPTION: SEQ ID NO:38:

Arg Pro Cys Pro Gln Cys Phe Val Gly Leu Met
 1               5                   10

(2) INFORMATION FOR SEQ ID NO:39:

(i) SEQUENCE CHARACTERISTICS:
  (A) LENGTH: 11 amino acids
  (B) TYPE: amino acid
  (D) TOPOLOGY: linear (ii) MOLECULE TYPE: protein (xi) SEQUENCE DESCRIPTION: SEQ ID NO:39:

Arg Pro Cys Pro Gln Cys Phe Tyr Ala Leu Met
 1               5                   10

(2) INFORMATION FOR SEQ ID NO:40:

(i) SEQUENCE CHARACTERISTICS:
  (A) LENGTH: 11 amino acids
  (B) TYPE: amino acid
  (D) TOPOLOGY: linear (ii) MOLECULE TYPE: protein (xi) SEQUENCE DESCRIPTION: SEQ ID NO:40:

Arg Pro Cys Pro Gln Cys Phe Tyr Pro Leu Met
 1               5                   10

(2) INFORMATION FOR SEQ ID NO:41:

(i) SEQUENCE CHARACTERISTICS:
  (A) LENGTH: 11 amino acids
  (B) TYPE: amino acid
  (D) TOPOLOGY: linear (ii) MOLECULE TYPE: protein (xi) SEQUENCE DESCRIPTION: SEQ ID NO:41:

Arg Pro Cys Pro Gln Cys Phe Tyr Gly Pro Met
 1               5                   10

(2) INFORMATION FOR SEQ ID NO:42:

(i) SEQUENCE CHARACTERISTICS:
  (A) LENGTH: 10 amino acids
  (B) TYPE: amino acid
  (D) TOPOLOGY: linear (ii) MOLECULE TYPE: protein (xi) SEQUENCE DESCRIPTION: SEQ ID NO:42:

Asp Met His Asp Cys Phe Cys Gly Leu Met
 1               5                   10

(2) INFORMATION FOR SEQ ID NO:43:

(i) SEQUENCE CHARACTERISTICS:
  (A) LENGTH: 10 amino acids
  (B) TYPE: amino acid
  (D) TOPOLOGY: linear (ii) MOLECULE TYPE: protein (ix) FEATURE:
  (B) LOCATION: 7...7

-continued (D) OTHER INFORMATION: where Xaa at position 7 is Me-Val (x i) SEQUENCE DESCRIPTION: SEQ ID NO:43:

Asp Met His Asp Phe Phe Xaa Gly Leu Met
1               5                   10

(2) INFORMATION FOR SEQ ID NO:44:

(i) SEQUENCE CHARACTERISTICS:
        (A) LENGTH: 10 amino acids
        (B) TYPE: amino acid
        (D) TOPOLOGY: linear (i i) MOLECULE TYPE: protein (x i) SEQUENCE DESCRIPTION: SEQ ID NO:44:

Asp Met His Asp Phe Phe Pro Gly Leu Met
1               5                   10

(2) INFORMATION FOR SEQ ID NO:45:

(i) SEQUENCE CHARACTERISTICS:
        (A) LENGTH: 6 amino acids
        (B) TYPE: amino acid
        (D) TOPOLOGY: linear (i i) MOLECULE TYPE: protein (i x) FEATURE:
        (B) LOCATION: 1...1
        (D) OTHER INFORMATION: where Xaa at position 1 is pGlu+

(x i) SEQUENCE DESCRIPTION: SEQ ID NO:45:

Xaa Phe Phe Pro Leu Met
1               5

(2) INFORMATION FOR SEQ ID NO:46:

(i) SEQUENCE CHARACTERISTICS:
        (A) LENGTH: 13 amino acids
        (B) TYPE: amino acid
        (D) TOPOLOGY: linear (i i) MOLECULE TYPE: protein (i x) FEATURE:
        (B) LOCATION: 1...1
        (D) OTHER INFORMATION: where Xaa at position 1 is pGlu
        (B) LOCATION: 4...4
        (D) OTHER INFORMATION: where Xaa at position 4 is Me-Phe
        (B) LOCATION: 11...11
        (D) OTHER INFORMATION: where Xaa at position 11 is Me-Phe (x i) SEQUENCE DESCRIPTION: SEQ ID NO:46:

Xaa Gln Phe Xaa Gly Leu Met Gly Phe Phe Xaa Leu Met
1               5                   10

(2) INFORMATION FOR SEQ ID NO:47:

(i) SEQUENCE CHARACTERISTICS:
        (A) LENGTH: 5 amino acids
        (B) TYPE: amino acid
        (D) TOPOLOGY: linear (i i) MOLECULE TYPE: protein (i x) FEATURE:
        (B) LOCATION: 5...5
        (D) OTHER INFORMATION: where Xaa at position 5 is Nle (x i) SEQUENCE DESCRIPTION: SEQ ID NO:47:

Phe Phe Gly Leu Xaa
1               5

(2) INFORMATION FOR SEQ ID NO:48:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:48:

Tyr Phe Gly Leu Met
1               5

(2) INFORMATION FOR SEQ ID NO:49:

(i) SEQUENCE CHARACTERISTICS:
        (A) LENGTH: 5 amino acids
        (B) TYPE: amino acid
        (D) TOPOLOGY: linear (ii) MOLECULE TYPE: protein (ix) FEATURE:
        (B) LOCATION: 5...5
        (D) OTHER INFORMATION: where Xaa at position 5 is ethionine (xi) SEQUENCE DESCRIPTION: SEQ ID NO:49:

Phe Phe Gly Leu Xaa
1               5

(2) INFORMATION FOR SEQ ID NO:50:

(i) SEQUENCE CHARACTERISTICS:
        (A) LENGTH: 7 amino acids
        (B) TYPE: amino acid
        (D) TOPOLOGY: linear (ii) MOLECULE TYPE: protein (ix) FEATURE:
        (B) LOCATION: 1...1
        (D) OTHER INFORMATION: where Xaa at position 1 is pGlu (B) LOCATION: 4...4
        (D) OTHER INFORMATION: where Xaa at position 4 is Me-Phe (B) LOCATION: 5...5
        (D) OTHER INFORMATION: where Xaa at position 5 is Sar (xi) SEQUENCE DESCRIPTION: SEQ ID NO:50:

Xaa Gln Phe Xaa Xaa Leu Met
1               5

(2) INFORMATION FOR SEQ ID NO:51:

(i) SEQUENCE CHARACTERISTICS:
        (A) LENGTH: 7 amino acids
        (B) TYPE: amino acid
        (D) TOPOLOGY: linear (ii) MOLECULE TYPE: protein (ix) FEATURE:
        (B) LOCATION: 4...4
        (D) OTHER INFORMATION: where Xaa at position 4 is Me-Phe (xi) SEQUENCE DESCRIPTION: SEQ ID NO:51:

Asp Asp Phe Xaa Gly Leu Met 1             5

(2) INFORMATION FOR SEQ ID NO:52:

(i) SEQUENCE CHARACTERISTICS:
        (A) LENGTH: 6 amino acids
        (B) TYPE: amino acid
        (D) TOPOLOGY: linear (ii) MOLECULE TYPE: protein (ix) FEATURE:
        (B) LOCATION: 1...1
        (D) OTHER INFORMATION: where Xaa at position 1 is N-Acetyl-Arg
        (B) LOCATION: 3...3
        (D) OTHER INFORMATION: where Xaa at position 3 is Me-Phe (xi) SEQUENCE DESCRIPTION: SEQ ID NO:52:

Xaa  Phe  Xaa  Gly  Leu  Met
1             5

(2) INFORMATION FOR SEQ ID NO:53:

(i) SEQUENCE CHARACTERISTICS:
        (A) LENGTH: 6 amino acids
        (B) TYPE: amino acid
        (D) TOPOLOGY: linear (ii) MOLECULE TYPE: protein (ix) FEATURE:
        (B) LOCATION: 1...1
        (D) OTHER INFORMATION: where Xaa at position 1 is pGlu (xi) SEQUENCE DESCRIPTION: SEQ ID NO:53:

Xaa  Phe  Phe  Pro  Leu  Met
1             5

(2) INFORMATION FOR SEQ ID NO:54:

(i) SEQUENCE CHARACTERISTICS:
        (A) LENGTH: 11 amino acids
        (B) TYPE: amino acid
        (D) TOPOLOGY: linear (ii) MOLECULE TYPE: protein (ix) FEATURE:
        (B) LOCATION: 7...7
        (D) OTHER INFORMATION: where Xaa at position 7 is p-Chloro-Phe
        (B) LOCATION: 8...8
        (D) OTHER INFORMATION: where Xaa at position 8 is p-Chloro-Phe (xi) SEQUENCE DESCRIPTION: SEQ ID NO:54:

Arg  Pro  Lys  Pro  Gln  Gln  Xaa  Xaa  Gly  Leu  Met
1             5                     10

(2) INFORMATION FOR SEQ ID NO:55:

(i) SEQUENCE CHARACTERISTICS:
        (A) LENGTH: 11 amino acids
        (B) TYPE: amino acid
        (D) TOPOLOGY: linear (ii) MOLECULE TYPE: protein (ix) FEATURE:
        (B) LOCATION: 9...9
        (D) OTHER INFORMATION: where Xaa at position 9 is Sar
        (B) LOCATION: 11...11
        (D) OTHER INFORMATION: where Xaa at position 11 is Met(O2)

(xi) SEQUENCE DESCRIPTION: SEQ ID NO:55:

Arg Pro Lys Pro Gln Gln Phe Phe Xaa Leu Xaa
1               5                   10

( 2 ) INFORMATION FOR SEQ ID NO:56:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( i x ) FEATURE:
        ( B ) LOCATION: 1...1
        ( D ) OTHER INFORMATION: where Xaa at position 1 is D-Ala ( x i ) SEQUENCE DESCRIPTION: SEQ ID NO:56:

Xaa Gln Gln Phe Phe Gly Leu Met
1               5

( 2 ) INFORMATION FOR SEQ ID NO:57:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:57:

Arg Pro Lys Pro Gln Gln Phe Phe
1               5

( 2 ) INFORMATION FOR SEQ ID NO:58:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

Arg Pro Lys Pro Gln Gln
1               5

( 2 ) INFORMATION FOR SEQ ID NO:59:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( x i ) SEQUENCE DESCRIPTION: SEQ ID NO:59:

Arg Pro Lys Pro Gln
1               5

( 2 ) INFORMATION FOR SEQ ID NO:60:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:60:

Lys Pro Gln Gln Phe Phe Gly Leu Met
1               5

( 2 ) INFORMATION FOR SEQ ID NO:61:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
        ( B ) LOCATION: 10...10
        ( D ) OTHER INFORMATION: where Xaa at location 10 is Me-Leu ( x i ) SEQUENCE DESCRIPTION: SEQ ID NO:61:

Arg Pro Lys Pro Gln Gln Phe Phe Gly Xaa Met
1               5                       10

( 2 ) INFORMATION FOR SEQ ID NO:62:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

Arg Pro Lys Pro Gln Gln Phe Phe Gly Pro Met
1               5                       10

( 2 ) INFORMATION FOR SEQ ID NO:63:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
        ( B ) LOCATION: 11...11
        ( D ) OTHER INFORMATION: where Xaa at position 11 is Me-Met ( x i ) SEQUENCE DESCRIPTION: SEQ ID NO:63:

Arg Pro Lys Pro Gln Gln Phe Phe Gly Leu Xaa
1               5                       10

( 2 ) INFORMATION FOR SEQ ID NO:64:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:64:

Arg Pro Lys Pro Gln Gln Phe Phe Gly Leu Pro
1               5                       10

( 2 ) INFORMATION FOR SEQ ID NO:65:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( i x ) FEATURE:
    ( B ) LOCATION: 9...9
    ( D ) OTHER INFORMATION: where Xaa at position 9 is Me-Gly ( x i ) SEQUENCE DESCRIPTION: SEQ ID NO:65:

```
Arg  Pro  Lys  Pro  Gln  Gln  Phe  Phe  Xaa  Leu  Met
 1                   5                        10
```

( 2 ) INFORMATION FOR SEQ ID NO:66:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( i x ) FEATURE:
    ( B ) LOCATION: 10...10
    ( D ) OTHER INFORMATION: where Xaa at position 10 is Me-Leu ( x i ) SEQUENCE DESCRIPTION: SEQ ID NO:66:

```
Arg  Pro  Lys  Pro  Gln  Gln  Phe  Phe  Gly  Xaa  Met
 1                   5                        10
```

( 2 ) INFORMATION FOR SEQ ID NO:67:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: protein ( i x ) FEATURE:
    ( B ) LOCATION: 11...11
    ( D ) OTHER INFORMATION: where Xaa at position 11 is Me-Met ( x i ) SEQUENCE DESCRIPTION: SEQ ID NO:67:

```
Arg  Pro  Lys  Pro  Gln  Gln  Phe  Phe  Gly  Pro  Xaa
 1                   5                        10
```

( 2 ) INFORMATION FOR SEQ ID NO:68:

( i ) SEQUENCE CHARACTERISTICS:
    ( A ) LENGTH: 38 amino acids
    ( B ) TYPE: amino acid
    ( D ) TOPOLOGY: linear ( i i ) MOLECULE TYPE: protein ( x i ) SEQUENCE DESCRIPTION: SEQ ID NO:68:

```
Asp  Ala  Glu  Phe  Arg  His  Asp  Ser  Gly  Tyr  Glu  Val  His  His  Gln  Lys
 1                   5                        10                       15
Leu  Val  Phe  Phe  Ala  Glu  Asp  Val  Gly  Ser  Asn  Lys  Gly  Ala  Ile  Ile
                    20                        25                       30
Gly  Leu  Met  Val  Gly  Gly
                    35
```

( 2 ) INFORMATION FOR SEQ ID NO:69:

( i ) SEQUENCE CHARACTERISTICS:
    ( A ) LENGTH: 40 amino acids
    ( B ) TYPE: amino acid
    ( D ) TOPOLOGY: linear ( i i ) MOLECULE TYPE: protein ( x i ) SEQUENCE DESCRIPTION: SEQ ID NO:69:

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
            35                  40

( 2 ) INFORMATION FOR SEQ ID NO:70:

( i ) SEQUENCE CHARACTERISTICS:
        ( A ) LENGTH: 43 amino acids
        ( B ) TYPE: amino acid
        ( D ) TOPOLOGY: linear ( i i ) MOLECULE TYPE: protein ( x i ) SEQUENCE DESCRIPTION: SEQ ID NO:70:

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Tyr
            35                  40

( 2 ) INFORMATION FOR SEQ ID NO:71:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:71:

Gly Ala Ile Ile Gly Leu Met
1               5

( 2 ) INFORMATION FOR SEQ ID NO:72:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: protein ( x i ) SEQUENCE DESCRIPTION: SEQ ID NO:72:

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40

( 2 ) INFORMATION FOR SEQ ID NO:73:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:73:

Glu Pro Ser Lys Asp Ala Phe Ile Gly Leu Met

-continued (2) INFORMATION FOR SEQ ID NO:74:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:74:

```
Asp  Met  His  Asp  Phe  Phe  Val  Gly  Leu  Met
 1              5                        10
```

(2) INFORMATION FOR SEQ ID NO:75:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:75:

```
His  Lys  Thr  Asp  Ser  Phe  Val  Gly  Leu  Met
 1              5                        10
```

(2) INFORMATION FOR SEQ ID NO:76:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:76:

```
Asp  Val  Pro  Lys  Ser  Asp  Gln  Phe  Val  Gly  Leu  Met
 1              5                        10
```

(2) INFORMATION FOR SEQ ID NO:77:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:77:

```
Arg  Pro  Lys  Pro  Gln  Gln  Phe  Phe  Gly  Leu  Met
 1              5                        10
```